(12) United States Patent
Kitamura (10) Patent No.: US 9,965,698 B2
(45) Date of Patent: May 8, 2018

(54) IMAGE PROCESSING APPARATUS, NON-TRANSITORY COMPUTER-READABLE RECORDING MEDIUM HAVING STORED THEREIN IMAGE PROCESSING PROGRAM, AND OPERATION METHOD OF IMAGE PROCESSING APPARATUS

(71) Applicant: FUJIFILM Corporation, Tokyo (JP)

(72) Inventor: Yoshiro Kitamura, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days. days.

(21) Appl. No.: 14/865,616

(22) Filed: Sep. 25, 2015

(65) Prior Publication Data

US 2016/0019435 A1 Jan. 21, 2016

Related U.S. Application Data (63) Continuation of application No. PCT/JP2014/001618, filed on Mar. 20, 2014.

(30) Foreign Application Priority Data

Mar. 27, 2013 (JP) ................. 2013-066092

(51) Int. Cl.
*G06K 9/52* (2006.01)
*G06K 9/62* (2006.01)
(Continued)

(52) U.S. Cl.
CPC ............ *G06K 9/52* (2013.01); *A61B 6/032* (2013.01); *A61B 6/503* (2013.01); *G06K 9/6267* (2013.01);
(Continued)

(58) Field of Classification Search
None
See application file for complete search history.

(56) References Cited

U.S. PATENT DOCUMENTS

| | | | |
|---|---|---|---|
| 2004/0184646 A1* | 9/2004 | Oosawa | G06K 9/00127 382/128 |
| 2006/0029275 A1 | 2/2006 | Li et al. | |
| 2012/0020528 A1 | 1/2012 | Yamada | |

FOREIGN PATENT DOCUMENTS

| | | |
|---|---|---|
| JP | 2006-053919 A | 2/2006 |
| JP | 2010-121945 A | 6/2010 |

(Continued)

OTHER PUBLICATIONS

Odry, B.—"Active contour approach for accurate quantitative airway analysis"—SPIE 2008, pp. 1-12.*
Kohli, P.—"Robust Higher Order Potentials for Enforcing Label Consistency"—IEEE 2008, pp. 1-8.*
Kohli, P.—"P3 & Beyond: Move Making Algorithms for Solving Higher Order Functions"—IEEE 2009, pp. 1645-1656.*

(Continued)

*Primary Examiner* — Bernard Krasnic
(74) *Attorney, Agent, or Firm* — Sughrue Mion, PLLC (57) ABSTRACT

When binary labeling is performed, an outline specification unit specifies a first outline present toward a target region and a second outline present toward a non-target region, and which have shapes similar to an outline of the target region. A voxel selection unit selects an N number of voxels constituting all of the first outline and the second outline. The energy setting unit sets N-order energy when a condition that all of the voxels of the first outline belong to the target region and all of the voxels of the second outline belong to the non-target region is satisfied smaller than the N-order energy when the condition is not satisfied. After then, labeling is performed by minimizing energy.

10 Claims, 9 Drawing Sheets

(51) Int. Cl.

| | |
|---|---|
| G06T 7/149 | (2017.01) |
| A61B 6/03 | (2006.01) |
| A61B 6/00 | (2006.01) |
| G06T 7/73 | (2017.01) |
| G06T 7/11 | (2017.01) |
| G06T 7/12 | (2017.01) |
| G06T 7/162 | (2017.01) |
| G06T 7/68 | (2017.01) |
| G06K 9/46 | (2006.01) |

(52) U.S. Cl.
CPC ............. *G06T 7/11* (2017.01); *G06T 7/12* (2017.01); *G06T 7/149* (2017.01); *G06T 7/162* (2017.01); *G06T 7/68* (2017.01); *G06T 7/73* (2017.01); *G06K 2009/4666* (2013.01); *G06T 2200/04* (2013.01); *G06T 2207/10081* (2013.01); *G06T 2207/20021* (2013.01); *G06T 2207/20072* (2013.01); *G06T 2207/20112* (2013.01); *G06T 2207/20116* (2013.01); *G06T 2207/30101* (2013.01); *G06T 2207/30172* (2013.01)

(56) References Cited

FOREIGN PATENT DOCUMENTS

| | | |
|---|---|---|
| JP | 4709290 B2 | 6/2011 |
| JP | 4717935 B2 | 7/2011 |
| JP | 2012-027713 A | 2/2012 |
| JP | 2013-020600 A | 1/2013 |

OTHER PUBLICATIONS

Kohli, P.—"Graph Cuts for Minimizing Robust Higher Order Potentials"—2008, pp. 1-9.*
Vladimir Kolmogorov et al., "What Energy Functions Can Be Minimized via Graph Cuts?", IEEE Transactions on PAMI, Feb. 2004, pp. 147-159, vol. 26, No. 2.
Carsten Rother et al., "Minimizing Sparse Higher Order Energy Functions of Discrete Variables", IEEE, CVPR, 2009, pp. 1382-1389.
Carsten Rother et al., "Optimizing Binary MRFs via Extended Roof Duality", IEEE, CVPR, 2007, pp. 1-8.
Max W.K. Law et al., "Three Dimensional Curvilinear Structure Detection Using Optimally Oriented Flux", Proceedings of ECCV, Part IV, LNCS 5305, 2008, pp. 368-382.
Vladimir Kolmogorov, "Convergent Tree-reweighted Message Passing for Energy Minimization", IEEE Transaction on PAMI, 2006, pp. 1-16, vol. 28, issue 10.
Yuri Boykov et al., "An Experimental Comparison of Min-Cut/Max-Flow Algorithms for Energy Minimization in Vision", IEEE Transaction on PAMI, Sep. 2004, pp. 1124-1137, vol. 26, No. 9.
Viet-Quoc Pham et al., "Image Segmentation from Bounding Shape without Using Appearance Model", The Transactions of the institute of Electronics, Information and Communication Engineers, 2011, pp. 1183-1193, vol. J94-D, No. 8.
Haruyuki Iwama et al., "Foreground, Shadow and Background Segmentation Based on Homography-Correspondence Pair", The Transactions of the institute of Electronics, Information and Communication Engineers, 2011, pp. 1300-1313, vol. J94-D, No. 8.
Written Opinion for PCT/JP2014/001618 dated Jun. 3, 2014.
International Search Report for PCT/JP2014/001618 dated Jun. 3, 2014.

* cited by examiner

IMAGE PROCESSING APPARATUS, NON-TRANSITORY COMPUTER-READABLE RECORDING MEDIUM HAVING STORED THEREIN IMAGE PROCESSING PROGRAM, AND OPERATION METHOD OF IMAGE PROCESSING APPARATUS

CROSS-REFERENCE TO RELATED APPLICATIONS

This application is a Continuation of PCT International Application No. PCT/JP2014/001618 filed on Mar. 20, 2014, which claims priority under 35 U.S.C. § 119(a) to Japanese Patent Application No. 2013-066092 filed on Mar. 27, 2013. Each of the above applications is hereby expressly incorporated by reference, in its entirety, into the present application.

BACKGROUND

The present disclosure relates to an image processing apparatus that segments an image into plural regions by using a discrete optimization method, such as graph cuts and QPBO (Quadratic Pseudo-Boolean Optimization), an image processing program and an operation method of the image processing apparatus.

Energy minimization using an algorithm for minimum cut of a graph (graph cuts) became widely applied to image processing in recent years. In particular, a method for efficiently solving an image segmentation (region segmentation) problem, as an energy minimization problem, has been proposed.

Graph cuts developed basically with respect to second order energy, which depends on two variables. Meanwhile, V. Kolmogorov and R. Zabih, proposed a method for minimizing submodular third order energy, which depends on three variables (for example, V. Kolmogorov and R. Zabih, "What Energy Functions Can Be Minimized via Graph Cuts?", IEEE TRANSACTIONS ON PAMI, Vol. 26, No. 2, pp. 147-159, 2004 (Non-Patent Document 1)).

Further, a method for solving a high order energy function of fourth order or higher by transforming the high order energy function to a second order energy function has been proposed. When all of coefficients of quadratic terms of the energy function after transformation are negative, the function is referred to as a submodular function, and a minimum solution is obtainable at high speed by using Max-Flow/Min-Cut algorithm. Meanwhile, when a positive value is included in coefficients of quadratic terms of the energy function after transformation (non-submodular), optimization of the original high order energy function is possible by minimization or obtainment of an approximate solution by using QPBO algorithm. As this energy function transformation, plural methods are known. For example, Rother et al. proposed this transformation (for example, C. Rother et al., "Minimizing Sparse Higher Order Energy Functions of Discrete Variables", IEEE, CVPR, pp. 1382-1389, 2009 (Non-Patent Document 2)).

Further, a method has been proposed in which a graph cut technique is used to extract a region of a target to be extracted. In the method, energy is set based on a distance from a closed curve representing an outline of the target, and segmentation into an object region and the other region is performed (for example, Japanese Unexamined Patent Publication No. 2012-027713 (Patent Document 1)).

SUMMARY

Non-Patent Document 1 and Non-Patent Document 2 disclose methods for obtaining solutions by transforming high order energy to second order energy. Patent Document 1 discloses a method for performing segmentation into a target region having a specific outline and the other region by setting energy based on the outline. Non-Patent Document 2 discloses setting high order energy for pixels in a rectangular window, as one of application examples of segmentation using high order energy. In this method, it is difficult to set sufficiently sparse high order energy. Therefore, there was a problem that a calculation amount was large.

In view of the foregoing circumstances, the present disclosure provides an image processing apparatus using high order energy, which is effective in segmentation, an image processing program and an operation method of the image processing apparatus.

An image processing apparatus of the present disclosure performs labeling by assigning a first variable representing a target region or a second variable representing a non-target region, which excludes the target region, to each voxel constituting image data by using an energy minimization method. The apparatus includes an outline specification means that specifies a first outline that is present toward the target region and a second outline that is present at a position facing the first outline with an outline of the target region between the first outline and the second outline, and which have shapes similar to the outline of the target region, a voxel selection means that selects an i ($\geq 1$) number of voxels forming the whole first outline and an (N–i) (N$\geq$4, N–i$\geq$1) number of voxels forming the whole second outline, an energy setting means that sets N-order energy when a condition that all of the i number of voxels of the first outline belong to the target region and all of the (N–i) number of voxels of the second outline belong to the non-target region is satisfied smaller than the N-order energy when the condition is not satisfied, and a labeling means that performs labeling by minimizing the N-order energy.

An image processing program of the present disclosure causes a computer to function as an image processing apparatus that performs labeling by assigning a first variable representing a target region or a second variable representing a non-target region, which excludes the target region, to each voxel constituting image data by using an energy minimization method. The program causes the computer to function as an outline specification means that specifies a first outline that is present toward the target region and a second outline that is present at a position facing the first outline with an outline of the target region between the first outline and the second outline, and which have shapes similar to the outline of the target region, a voxel selection means that selects an i ($\geq 1$) number of voxels forming the whole first outline and an (N–i) (N$\geq$4, N–i$\geq$1) number of voxels forming the whole second outline, an energy setting means that sets N-order energy when a condition that all of the i number of voxels of the first outline belong to the target region and all of the (N–i) number of voxels of the second outline belong to the non-target region is satisfied smaller than the N-order energy when the condition is not satisfied, and a labeling means that performs labeling by minimizing the N-order energy.

An operation method of the present disclosure is an operation method of an image processing apparatus that includes an outline specification means, a voxel selection means, an energy setting means and a labeling means, and performs labeling by assigning a first variable representing a target region or a second variable representing a non-target region, which excludes the target region, to each voxel constituting image data by using an energy minimization method. The operation method includes an outline specification step in which the outline specification means specifies a first outline that is present toward the target region and a second outline that is present at a position facing the first outline with an outline of the target region between the first outline and the second outline, and which have shapes similar to the outline of the target region, a voxel selection step in which the voxel selection means selects an i ($\geq 1$) number of voxels forming the whole first outline and an (N−i) (N$\geq$4, N−i$\geq$1) number of voxels forming the whole second outline, an energy setting step in which the energy setting means sets N-order energy when a condition that all of the i number of voxels of the first outline belong to the target region and all of the (N−i) number of voxels of the second outline belong to the non-target region is satisfied smaller than the N-order energy when the condition is not satisfied, and a labeling step in which the labeling means performs labeling by minimizing the N-order energy.

The "shapes similar to the outline of the target region" refer to shapes resembling the shape of the outline of the target region. It is desirable that the first outline is located away from the outline of the target region toward the inside of the target region by an approximately constant distance. It is desirable that the second outline is located away from the outline of the target region toward the outside of the target region (toward the non-target region) by an approximately constant distance.

It is desirable that the outline specification means specifies the first outline and the second outline in such a manner that the first outline and the second outline are apart from each other by a predetermined distance.

An outline estimation means that estimates the outline of the target region by using the image data may be further provided. The outline specification means may specify the first outline and the second outline based on the estimated outline.

The outline estimation means may estimate the outline of the target region based on the image data by using differential filtering that can detect an edge.

The outline estimation means may estimate the outline of the target region based on the image data by using a shape model represented by a predetermined parameter.

It is desirable that the energy setting means sets a same value for all the N-order energy in every case when the condition is not satisfied.

Further, the labeling means may use QPBO algorithm to minimize energy.

DESCRIPTION OF THE PREFERRED EMBODIMENTS

Hereinafter, embodiments of the present disclosure will be described in detail with reference to the drawings. The embodiments of the present disclosure will be described about a region segmentation method performed by assigning a first variable representing a target region or a second variable representing a non-target region, which excludes the target region, to each voxel in an image by using a graph cut method. An image processing apparatus of the present disclosure is achievable by loading and executing an image processing program in a computer. The image processing program is distributed by being stored in a storage medium, such as a CD-ROM, and installed in a computer from the storage medium, such as a CD-ROM. Alternatively, the image processing program is distributed through a network, such as the Internet, and installed in a computer.

Figure 1:
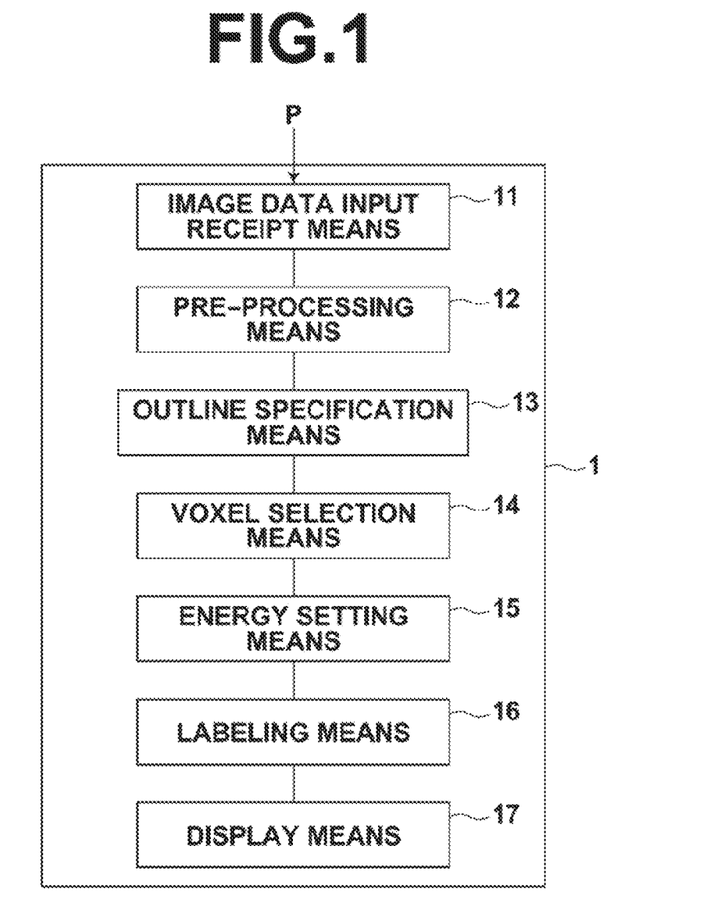
FIG. 1 is a block diagram illustrating the configuration of a first image processing apparatus.
Figure 2:
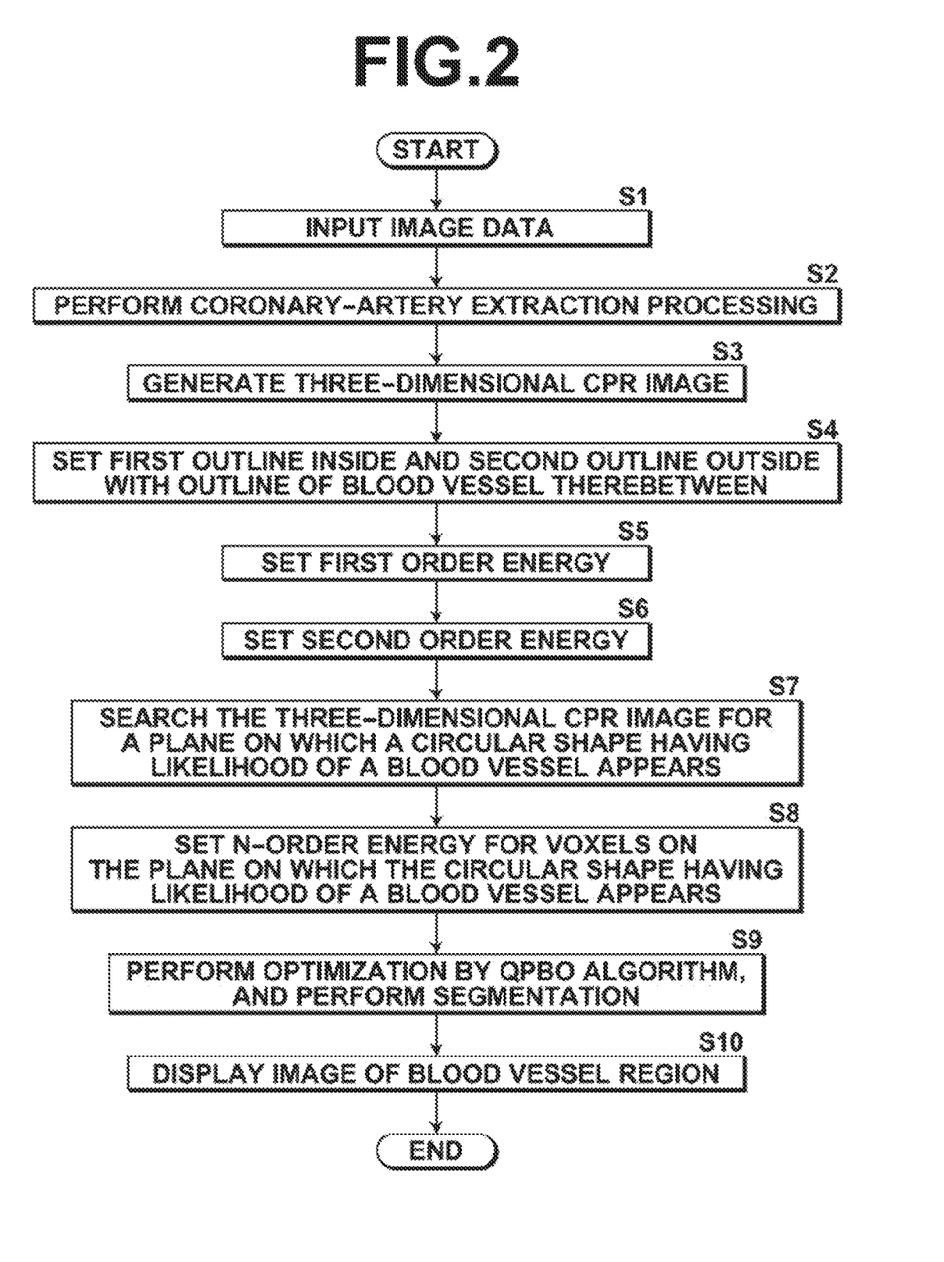
FIG. 2 is a flow chart showing a flow of image processing.

FIG. 1 is a block diagram illustrating the configuration of a first image processing apparatus 1 according to the present disclosure. FIG. 2 is a flow chart showing a flow of processing by the image processing apparatus 1 according to the present disclosure.

As illustrated in FIG. 1, the image processing apparatus 1 includes an image data input receipt means 11, a pre-processing means 12, an outline specification means 13, a voxel selection means 14, an energy setting means 15, a labeling means 16 and a display means 17.

The image data input receipt means 11 receives an input of image data P on which image processing is to be performed, and stores image data P in a storage device (S1). Image data P are plain X-ray radiographic images, tomographic images imaged by a CT scanner and an MRI apparatus, and the like. Plural organs or tissues or a lesion has been imaged in image data P.

Next, processing performed when image data P are a contrast enhanced CT image (voxel data) of a heart, and an outline of coronary arteries is to be extracted from the contrast enhanced CT image of the heart will be described.

Figure 3:
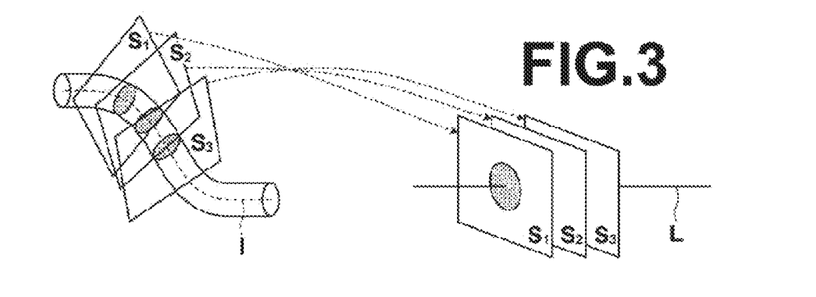
FIG. 3 is a diagram for explaining a method for generating a three-dimensional CPR image based on a contrast enhanced CT image of a heart.
Figure 4:
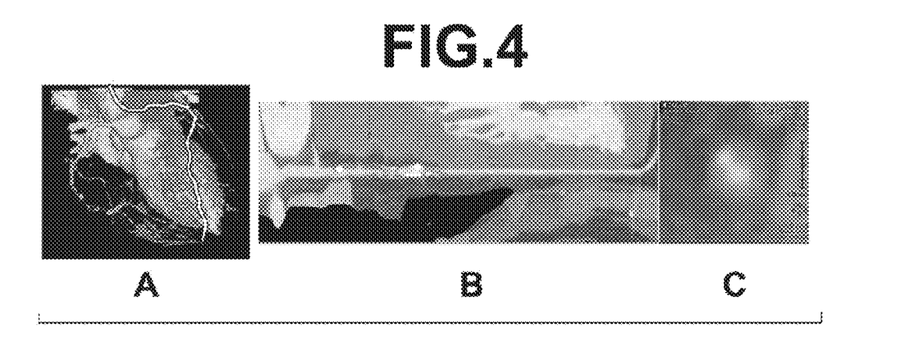
FIG. 4 is a diagram illustrating an example of a three-dimensional CPR image generated based on a contrast enhanced CT image of a heart.

The pre-processing means 12 extracts center line 1 (broken line) of the coronary arteries from the contrast enhanced CT image, as illustrated in FIG. 3, by known coronary artery extraction processing (S2). Various methods, such as methods disclosed in Japanese Patent No. 4709290 and Japanese Patent No. 4717935, have been proposed as methods for coronary artery extraction processing. Tomographic images $S_1$, $S_2$, $S_3$, which are orthogonal to the center line of a blood vessel, are generated from the contrast enhanced CT image (a left diagram in FIG. 3). A three-dimensional CPR image is generated by arranging these tomographic images $S_1$, $S_2$, $S_3$ in such a manner that the center coordinates of the blood vessel in these tomographic images are positioned on straight line L (a right diagram in FIG. 3) (S3). FIG. 4, Sections A through C illustrate an example in which a three-dimensional CPR image (Sections B and C in FIG. 4, and Section C is a cross section of the blood vessel) has been generated from a contrast enhanced image of the heart (Section A in FIG. 4, and processing is performed on the blood vessel in white).

The three-dimensional CPR image generated by the pre-processing means 12 is segmented into two regions of a background region and a blood vessel region.

First, a graph cut method, which is used to segment an image into two regions, will be described. Segmentation of an image is solvable by minimizing an energy function composed of first order energy $E^i$ and second order energy $E^{ij}$ represented by the following expression (1) when a variable $\{x_1, x_2, \ldots, x_n\}$ corresponding to each voxel in the image is defined as $x \in \{1, 0\}$.

[Expression 1]

$$E(x_1, \ldots, x_n) = \sum_{i \in V} E^i(x_i) + \sum_{i \in V, j \in Ni} E^{ij}(x_i, x_j), \quad (1)$$

where

V is a set of voxels constituting the image, and Ni is a set of voxels adjacent to voxel i.

First order energy $E^i(x_i)$ in Expression (1) is a value depending only on a label assigned to each voxel, and is directly influenced by the label assigned to each voxel. The sum in the second term defines energy in such a manner to reflect prior knowledge as to what kind of relationship labels assigned to adjacent voxels should have.

Figure 5:
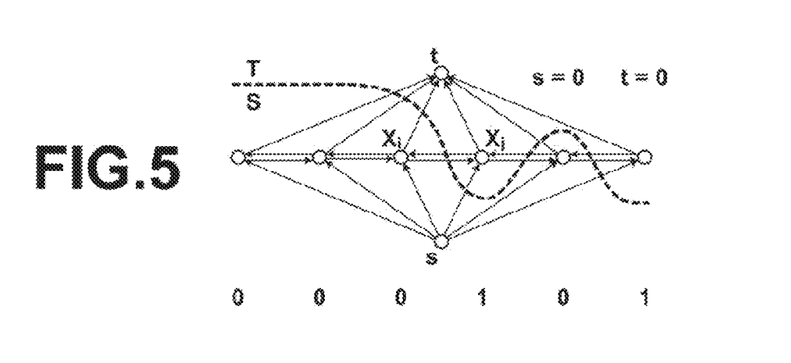
FIG. 5 is an example of a graph when classification into two classes is performed.

As illustrated in FIG. 5, a directional graph representing Expression (1) is set. The graph includes vertex $x_i$ (or vertex $x_j$) corresponding to each voxel, and further includes two vertices s (=0) and t (=1) corresponding to respective labels. With respect to each of vertex $x_i$ and vertex $x_j$, the directional graph is composed of an edge from vertex s to vertex $x_i$ or $x_j$, an edge from vertex $x_i$ or $x_j$ to vertex t and an edge between vertices $x_i$, $x_j$ corresponding to adjacent voxels. Further, first order energy $E^i(x_i)$ or $E^i(x_j)$ is defined for the edge from vertex s to vertex $x_i$ or $x_j$ and the edge from vertex $x_i$ or $x_j$ to vertex t. Second order energy $E^{ij}(x_i, x_j)$ is defined for the edge connecting the vertices corresponding to adjacent voxels. The energy (weight) of each edge should be determined in such a manner that a label giving minimum energy and minimum cut correspond to each other to obtain a label for each voxel by minimizing energy E(x) represented by Expression (1).

For example, if second order energy $E^{ij}(x_i, x_j)$ is given by the following expression:

[Expression 2]

$$\begin{bmatrix} E^{ij}(0,0) & E^{ij}(0,1) \\ E^{ij}(1,0) & E^{ij}(0,1) \end{bmatrix} = \begin{bmatrix} a & b \\ c & d \end{bmatrix}, \quad (2)$$

second order energy $E^{ij}$ expressed by a pseudo-Boolean expression is represented by the following quadratic expression:

[Expression 3]

$$E^{ij}(x_i, x_j) = a(1-x_i)(1-x_j) + b(1-x_i)x_j + cx_i(1-x_j) + dx_ix_j \quad (3)$$

In a pseudo-boolean expression, when all of coefficients in quadratic terms are negative, the expression is referred to as a submodular expression, and a minimum solution is obtainable at high speed by using Max-Flow/Min-Cut algorithm. Meanwhile, when a positive value is included in coefficients of the quadratic terms in the expression (i.e., non-submodular), minimization or obtainment of a semi-optimal solution is possible by using QPBO algorithm (please refer to C. Rother et al., "Optimizing Binary MRFs via Extended Roof Duality", IEEE, CVPR, pp. 1-8, 2007, for details).

Further, regarding an energy function of third order or higher, after the energy function of third order or higher is transformed into a second order energy function, the second order energy function is optimized by QPBO algorithm, which has been conventionally known. In this manner, it is possible to optimize the original high order function of third order or higher.

For example, Rother et al. disclosed a method for transforming a graph by adding auxiliary variables $z_0$, $z_1$. For example, if a third order energy function is given by the following expression:

[Expression 4]

$$\begin{bmatrix} E^{ijk}(0,0,0,) & E^{ijk}(0,0,1) \\ E^{ijk}(0,1,0) & E^{ijk}(0,1,1) \\ E^{ijkj}(1,0,0) & E^{ijk}(1,0,1) \\ E^{ijk}(1,1,0) & E^{ijk}(1,1,1) \end{bmatrix} = \begin{bmatrix} \theta & \theta \\ \theta & \theta \\ \theta & \theta \\ \theta & \theta \end{bmatrix}, \quad (4)$$

this third order energy $E^{ijk}$ expressed by a pseudo-boolean expression is represented by the following quadratic expression:

[Expression 5]

$$E^{ijk}(x_i, x_j, x_k) = \theta z_0 + \theta(1 - z_1) - \quad (5)$$
$$\theta z_0(1 - z_1) + \theta \sum_{a \in \{i,j,k\}} (1 - z_0)x_a + \theta \sum_{a \in \{i,j,k\}} z_1(1 - x_a)$$

$$z_0, z_1 \in \{1, 0\}.$$

Figure 6:
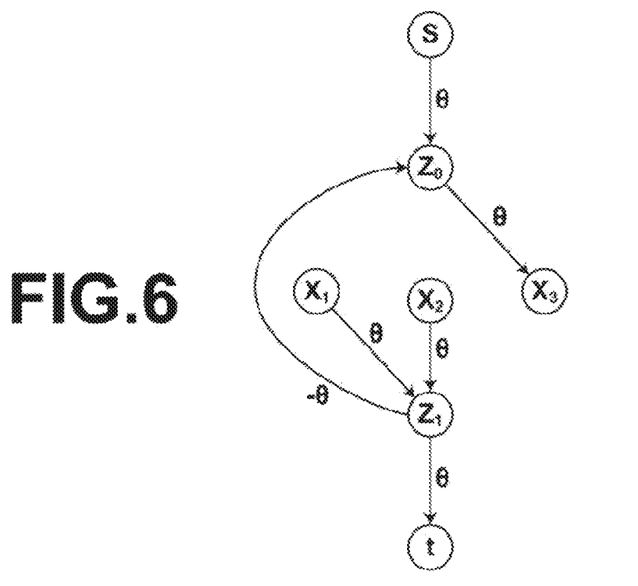
FIG. 6 is an example of a graph representing a quadratic expression in which high order energy has been transformed by pseudo-boolean function.

FIG. 6 illustrates a graph representing this transformation. After transformation is performed in this manner, a solution is obtained by performing minimization including the auxiliary variables. A solution obtainable as a result is equal to the solution of the original high order function (please refer to C. Rother et al., "Minimizing Sparse Higher Order Energy Functions of Discrete Variables", IEEE, CVPR, pp. 1382-1389, 2009, for details).

A solution is obtainable by performing similar transformation also for energy of fourth order or higher. This transformation needs to be performed for each different value of elements in a combination table of high order energy. In a complicated case, the number of auxiliary variables to be added is large, and optimization becomes difficult. However, when energy is sparse, for example, when only a specific value is small as in Expression (4), transformation should be performed only on elements having relatively small energy. Therefore, a problem after transformation is relatively simple, and a solution is obtainable in a practically acceptable calculation time period.

Next, a method for performing segmentation into a target region, in which a target having a known shape is present, and a region other than the target region (a non-target region) by using energy of fourth order or higher will be described. In the following descriptions, the target is a blood vessel, and a non-target is a background.

Figure 7:
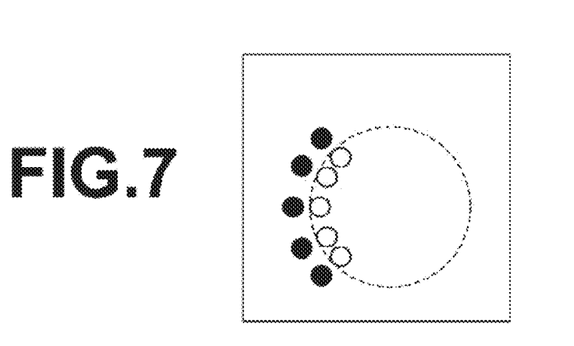
FIG. 7 is a diagram for explaining a cross-sectional shape of a blood vessel.

As illustrated in FIG. 7, the cross-sectional shape of a blood vessel is substantially circular. When a circle (a broken line) is applied to the outline of the blood vessel in an image, the inside of the outline of the circle is a blood vessel region, and the outside of the outline of the circle is a background region.

When representation by second order energy is performed, segmentation into the target region and the background region is possible by performing graph cut by setting small energy only for a combination of two voxels, one of which located in the background region has the value of 0 while the other voxel located in the blood vessel region has the value of 1.

Figure 8:
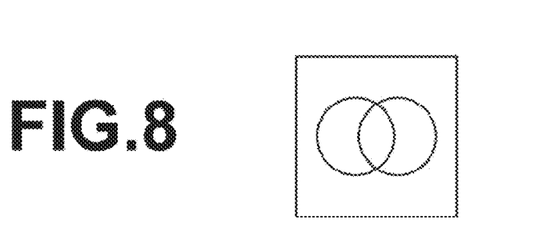
FIG. 8 is a diagram illustrating an example of a shape of a blood vessel region appearing in an image.
Figure 9:
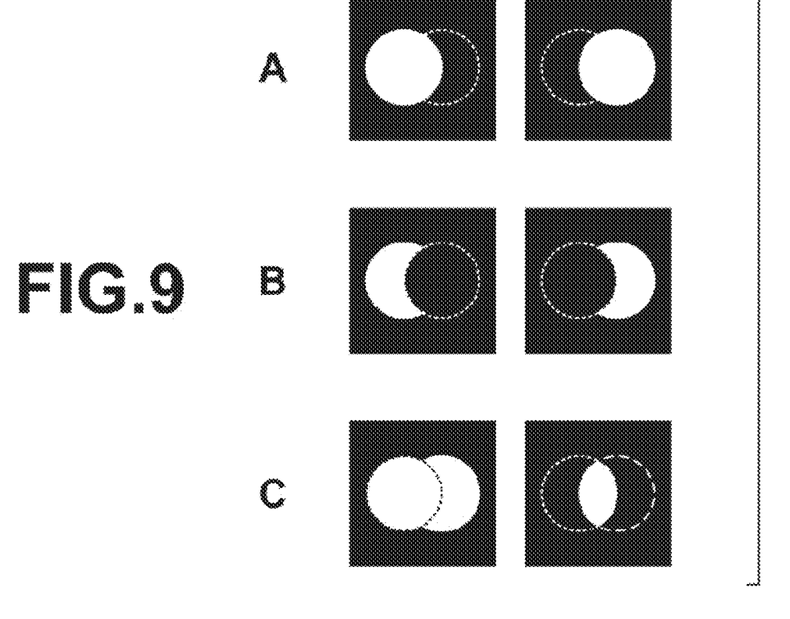
FIG. 9 is a diagram for explaining patterns in which a blood vessel region is separated from a background region.
Figure 10:
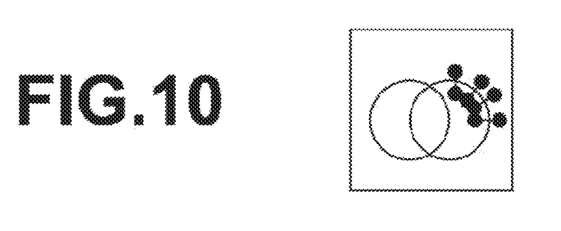
FIG. 10 is a diagram for explaining setting of second order energy.

A case in which energy is set in a state in which the outlines of two circles overlap with each other, as illustrated in FIG. 8, will be considered. At this time, when segmentation into the blood vessel region and the background region is performed by setting second order energy in the outline of the circle, there is a possibility that segmentation is performed in six patterns, as illustrated in FIG. 9, Sections A through C. As illustrated in FIG. 9, Section A, there is a case in which the inside of a left or right circle (a white part) is segmented, as a blood vessel, and separated from the background (a black part). As illustrated in FIG. 9, Section B, there is a case in which the inside of one of crescent shapes (a white part) is segmented, as a blood vessel. Further, there is a case in which a shape as illustrated in FIG. 9, Section C is segmented. Regarding second order energy, it is assumed that small energy is set when two voxels are present with the outline of the circle therebetween (please refer to FIG. 10). In both of the patterns illustrated in FIG. 9, Sections A and B, the sum of energy becomes smaller in proportion to the length of the outline of the circle. Therefore, the possibilities of occurrence of segmentation into patterns illustrated in FIG. 9, Sections A and B, and in which the outlines have the same length, are the same. Further, the sum of energy is relatively small also in the pattern illustrated in FIG. 9, Section C. Therefore, that is one of candidates for a solution. However, segmentation into patterns as illustrated in FIG. 9, Sections B and C is not desirable when the feature that the shape of a blood vessel is substantially circular is considered.

Therefore, N-order energy using voxel values of N ($\geq 4$) number of voxels, as variables, is used in addition to first order energy and second order energy to perform segmentation of the blood vessel region in a shape closer to a circle. In N-order energy, small energy is set only for a combination of a voxel having the value of 0, and which is located in the background around the outline of the circle having a size closer to the size of the blood vessel (● in FIG. 7) and a voxel having the value of 1, and which is located in the blood vessel around the outline (○ in FIG. 7). Since circles overlap with each other, when N-order energy of one of the two circles becomes smaller, energy of the other circle does not become smaller. Since this operation exclusively selects one of the circles, the blood vessel region having a shape close to a circle is segmented from the image.

Energy function E in which high order energy of fourth order or higher has been added is defined by the following expression:

[Expression 6]

$$E(x_1, \ldots, x_n) = \sum_{i \in V} E^i(x_i) + \sum_{i \in V, j \in Ni} E^{ij}(x_i, x_j) + \sum_{c \in C} E^c(X_c). \quad (6)$$

Here, c is a set of voxels constituting high order energy, and Xc is a vector composed of binary variables (0 or 1) of related voxels. C represents a set of c. Here, the order of each c may be different from each other. For example, the number of voxels related to a large circle is large, and the number of voxels related to a small circle is small.

Figure 11:
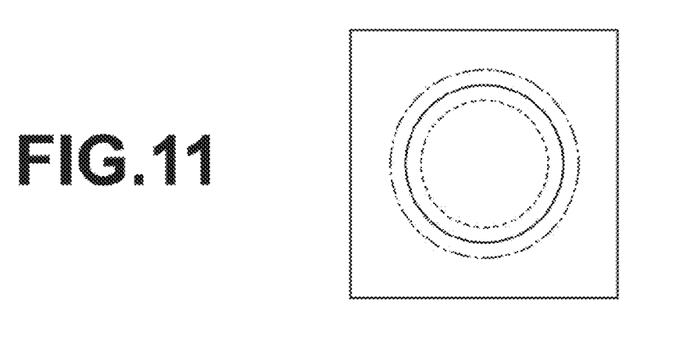
FIG. 11 is a diagram illustrating relationships among an outline of a target region, a first outline and a second outline.

First, the outline specification means 13 specifies an inside outline and an outside outline of the blood vessel (target) region. Specifically, as illustrated in FIG. 11, the outline specification means 13 specifies a first outline (a broken line) that is present toward the blood vessel (target) region with the outline (a solid line) of the blood vessel between the first outline and a second outline and the second outline (a dot dashed line) that is present toward the background (non-target) region at a position facing the first outline with the outline of the blood vessel between the first outline and the second outline. The shape of the first outline and the shape of the second outline are similar to the shape of the outline of the blood vessel. The outline of the blood vessel is substantially circular. Therefore, a circle in a size close to the size of the blood vessel is set. Further, a circle of the first outline and a circle of the second outline are set toward the inside of the circle and toward the outside of the circle, respectively.

Figure 12:
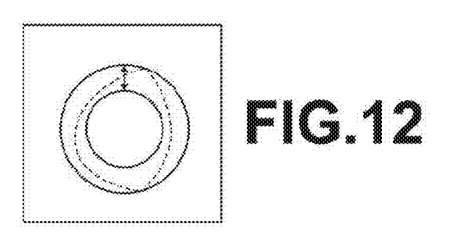
FIG. 12 is a diagram illustrating an example in which the first outline and the second outline are apart from each other.

However, if segmentation is performed constantly by using the shape of the circle having exactly the same size as the blood vessel, that is inconvenient as flexibility is low. Since the blood vessel appears in an actual image not always as a completely circular shape but sometimes as a slightly deformed circle. Therefore, it is desirable to obtain an outline according to an actual image. Therefore, as illustrated in FIG. 12, a space is provided between the first outline toward the blood vessel region (inside circle) and the second outline toward the background region (outside circle) so that the first outline and the second outline are apart from each other by a predetermined distance (S4). Then, even if the outline (the broken line) is flexibly set, the condition of high order energy is satisfied as long as the outline is set within the space between the outlines, and energy is small.

Figure 19:
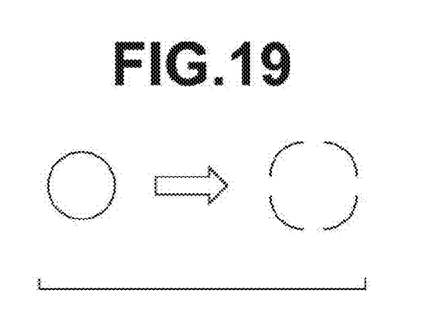
FIG. 19 is a diagram for explaining a method for defining a circle of the outline of the target region by plural arcs.

In other words, the outline is flexibly selected in the range satisfying the condition of high order energy in such a manner that second order energy is minimized. Further, instead of setting a complete circle, the circle of the first outline and the circle of the second outline may be divided, and plural arcs may be set, as illustrated in FIG. 19. When the circles are divided in this manner, an effect of reducing energy is achievable even if the pattern of only a part of the circle coincides. Therefore, a more flexible segmentation result is obtainable.

Figure 13:
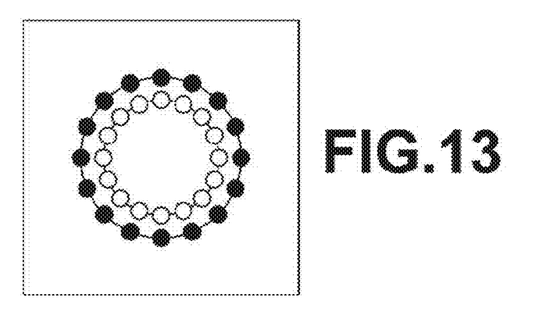
FIG. 13 is a diagram for explaining a method for selecting voxels on the first outline and voxels on the second outline.

Next, the voxel selection means 14 searches the three-dimensional CPR image for a position at which a shape having a likelihood of a blood vessel appears, and selects an i number of voxels on the first outline and an N−i number of voxels on the second outline, as illustrated in FIG. 13.

The energy setting means 15 sets high order energy together with first order energy and second order energy in a graph. The first order energy is set for an edge from vertex s (=0: background) to vertex $x_i$ and an edge from vertex $x_i$ to vertex t (=1: a blood vessel). When the value of each voxel has a likelihood of a blood vessel, smaller energy is set for the edge from vertex s to vertex $x_i$ than energy set for the edge from vertex $x_i$ to vertex t. When the value of each voxel has a likelihood of a background, smaller energy is set for the edge from vertex $x_i$ to vertex t than energy set for the edge from vertex s to vertex $x_i$ (S5). Second order energy is set for an edge between vertices $x_i$, $x_j$ corresponding to adjacent voxels, and smaller energy is set as a difference between voxel values of the adjacent voxels is larger (S6).

Further, the energy setting means 15 sets high order energy by identifying a position at which a shape having a likelihood of a circle appears in the three-dimensional CPR image to efficiently set high order energy. When all of i number of voxels of the first outline have voxel values having a likelihood of a blood vessel and all of (N−i) number of voxels of the second outline have voxel values having a likelihood of a background, the condition as outlines are satisfied. Therefore, when these conditions are satisfied, small energy (the weight has a negative coefficient, and the absolute value is large) is set for high order energy. When these conditions are not satisfied, larger energy is set for N-order energy, compared with a case in which these conditions are satisfied.

Figure 14:
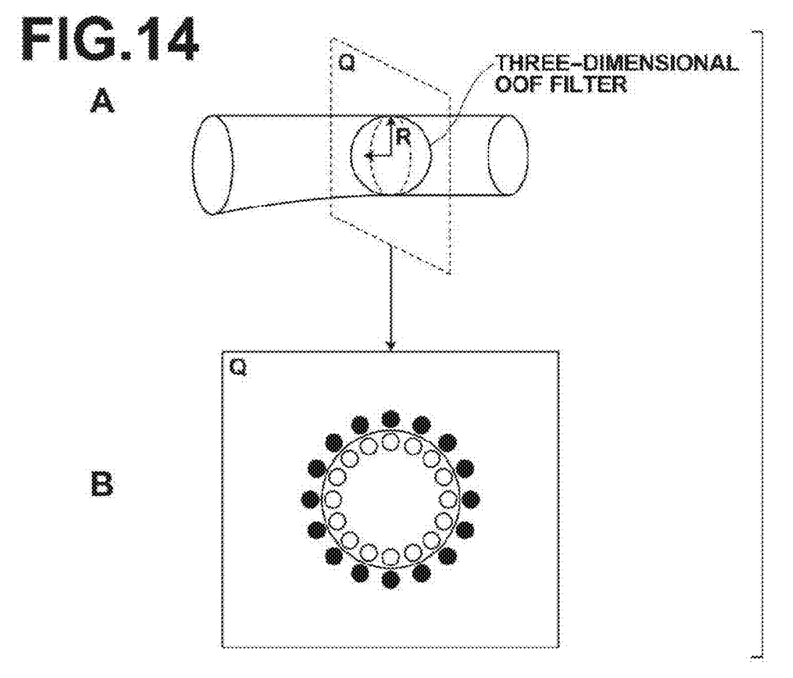
FIG. 14 is a diagram for explaining a circle having a likelihood of a blood vessel detected by using a three-dimensional OOF filter and a method for setting N-order energy.
Figure 15:
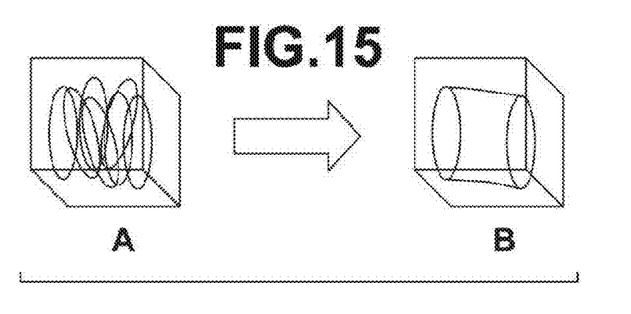
FIG. 15 is a diagram for explaining a method for performing segmentation of a blood vessel region based on plural circles that have been detected from a three-dimensional CPR image.

A three-dimensional OOF filter is used to identify a position at which circular N-order energy is set. The three-dimensional OOF filter has a spherical filter shape (a circular shape in a two-dimensional cross section) with radius R. As illustrated in FIG. 14, Section A, a response appears at a position at which a circle (a broken line) with radius R appears. Therefore, the three-dimensional OOF filter is applied to each position in three-dimensional CPR image P, and a position at which a shape having a likelihood of a circle appears is identified in the three-dimensional CPR image. Further, the three-dimensional OOF filter may calculate second order partial differential on the surface of a sphere, and calculate the likelihood of a circular cylindrical structure based on three eigenvalues obtained by performing eigendecomposition on the matrix of second order partial differential. When a circular cylindrical structure is present at a position to which the three-dimension OOF filter has been applied, two of three eigenvalues are large, and one of the three eigenvalues is a value close to zero. The eigenvalue having a value closest to zero among three eigenvalues obtained at the same time corresponds to main axis t of the circular cylindrical structure (a direction in which the blood vessel runs). An image having a likelihood of the outline of a blood vessel in a predetermined size is present on plane Q orthogonal to this main axis (regarding the three-dimension OOF filter, please refer to M. W. K. Law and A. C. S. Chung, "Three Dimensional Curvilinear Structure Detection Using Optimally Oriented Flux", Proceedings of ECCV, Part IV, LNCS 5305, pp. 368-382, 2008 for details). Plane Q on which such a circle appears is detected by filtering processing (S7). Since the accurate size of the blood vessel is not known in advance, detection is performed by using the OOF filter corresponding to circles in various sizes. FIG. 15, Sections A, B illustrate a manner in which circles are detected at plural positions by applying the three-dimensional OOF filter to each position in the three-dimensional CPR image.

As illustrated in FIG. 14, Section B, the voxel selection means 14 selects N-number of voxels on this plane Q, and the energy setting means 15 sets N-order energy (S8). Three-dimensional CPR image P is scanned with the three-dimensional OOF filter, and high order energy is set on plane Q at a position at which a response is high in such a manner that a value is relatively smaller when the selected N number voxels satisfy the condition of the outlines. Meanwhile, when N number of voxels selected on plane Q at a position at which the response of the three-dimensional OOF filter is low satisfy the condition of the outlines, N-order energy is set in such a manner that the N-order energy is larger than a case in which N-number of voxels selected on plane Q at a position at which the response is high satisfy the condition of the outlines, and also that the N-order energy is smaller than high order energy when the condition of a circle is not satisfied. For example, at a position at which the response of the three-dimensional OOF filter is high, large negative energy (the coefficient is negative, and the absolute value is large) is set for N-order energy when the condition of the outlines is satisfied. At a position at which the response of the three-dimensional OOF filter is low, small negative energy (the coefficient is negative, and the absolute value is small) is set for N-order energy when the condition of the outlines is satisfied.

The magnitude of energy is changed adaptively, as described above, because it has been known that the possibility that a circle is present is higher as the response of the filter is higher. Alternatively, it is possible to statistically calculate possibility based on data. For example, when data of a correct solution representing how segmentation should be performed on the blood vessel are present, the probability of a case in which N-order energy is smaller with respect the response of the three-dimensional OOF filter may be statistically calculated (learned) in advance, and the weight of energy may be set based on the probability. It is possible to calculate this probability as a ratio at which a combination of labels when N-order energy set by the aforementioned processing is small coincides with labels of data of the correct solution.

When the condition of the outline is not satisfied, the energy setting means 15 may set the same value for all N-order energy. When the condition of the outline is not satisfied, if the same value is set for energy in this manner, energy becomes sparse. Therefore, transformation from high order to low order is possible by using a small number of additional variables, and a solution is obtainable at relatively high speed.

The labeling means 16 transforms set high order (third order or higher) energy to a second order energy function. After then, the labeling means 16 optimizes the second order energy function by conventionally known QPBO algorithm, and performs segmentation into two regions of a blood vessel region and a background region (S9).

Figure 16:
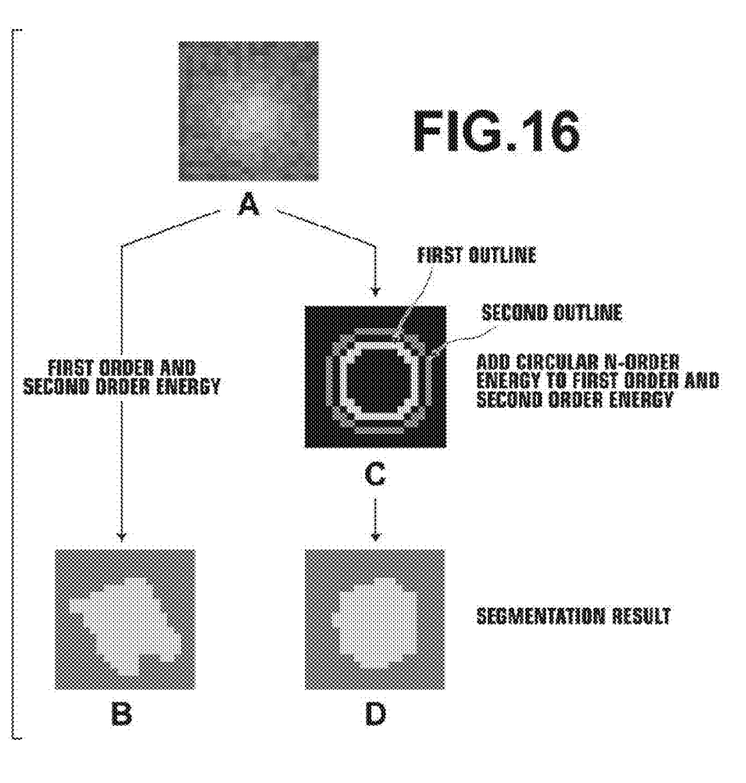
FIG. 16 is a diagram for explaining a difference between extraction of a blood vessel region by using a conventional method and extraction of a blood vessel region by using a method of the present disclosure.

Here, an effect achievable by setting circular high order energy will be described. When graph cut processing is performed on two-dimensional original image illustrated in FIG. 16, Section A by setting conventional two-dimensional energy, a greatly deformed circular shape is extracted, as illustrated in FIG. 16, Section B. Meanwhile, when circular high order energy is set, as illustrated in FIG. 16, Section C, segmentation into a shape close to a circular shape is performed, as illustrated in FIG. 16, Section D.

When circular high order energy is set as described above, segmentation of a blood vessel region is performed in such a manner that circular shapes (FIG. 15, Section A), which have been extracted, continue three-dimensionally (FIG. 15, Section B), as illustrated in FIG. 15, Sections A, B. Further, it is possible to prevent segmentation of a shape deviating from a circular shape.

The display means 17 displays an image of only the blood vessel based on the result by the labeling means 16 on the display device (S10).

In the above descriptions, a case in which high order energy is set for an object, such as the blood vessel, the shape of the outline of which is circular has been described. The shape of the outline for which high order energy is set may be any kind of shape. Voxels on a first outline, which is located toward the target region, and a second outline, which is located toward the non-target region, with various kinds of outline therebetween are selected. Then, high order energy when all of the voxels on the first outline belong to the target region and all of the voxels on the second outline belong to the non-target region is set smaller than a case in which these conditions are not satisfied.

It is desirable that the first outline is away from the outline of the target region toward the inside (toward the target region) constantly by an approximately constant distance in such a manner that the first outline is similar to the outline of the target region. It is desirable that the second outline is away from the outline of the target region toward the outside (toward the non-target region) constantly by an approximately constant distance in such a manner that the second outline is similar to the outline of the target region. However, the first and second outlines may be specified in such a manner that a distance from the outline of the target region differs within a predetermined range of error.

Figure 17A:
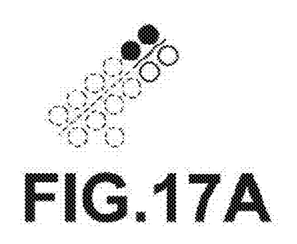
FIG. 17A is a diagram for explaining the shape of a straight line on which N-order energy is set and a method for selecting voxels constituting the shape.
Figure 17B:
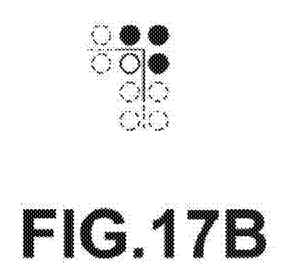
FIG. 17B is a diagram for explaining the shape of a corner on which N-order energy is set and a method for selecting voxels constituting the shape.

As illustrated in FIGS. 17A and 17B, if at least four voxels are used to constitute an outline, and at least one voxel is present at least on the first outline or the second outline, it is possible specify the shape of the outline. FIG. 17A illustrates an example in which segmentation into a target region and a non-target region is performed along a straight line. FIG. 17B illustrates an example in which segmentation into a target region and a non-target region is performed in a shape including a corner. Besides, it is possible to specify various shapes, such as a triangle and a rectangle. Alternatively, a surface or a curved surface in a three-dimensional image may be detected by specifying the shape of the surface or the curved surface, and segmentation may be performed.

In the above descriptions, a case in which a shape, such as the blood vessel, is known in advance has been described. Alternatively, as in the case of a second image processing apparatus 1a, illustrated in FIG. 18, an outline estimation means 18, which estimates the outline of a target region by using image data P, may be provided.

Figure 18:
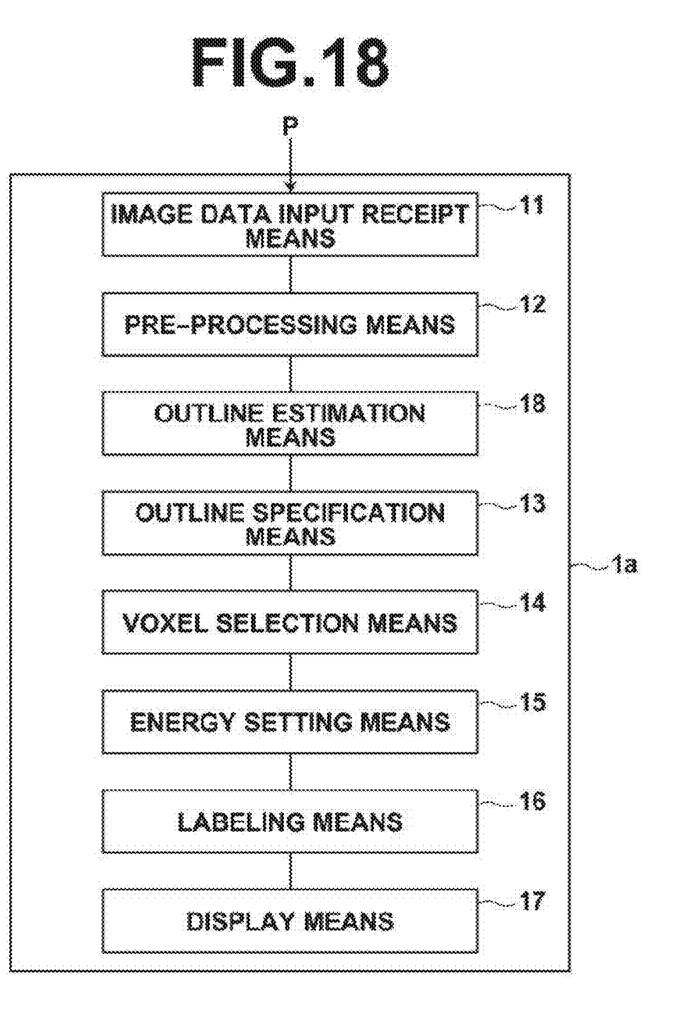
FIG. 18 is a block diagram illustrating the configuration of a second image processing apparatus.

The outline estimation means 18 may use differential filtering, in which an edge is detectable, as a method for estimating the outline. The response of the differential filter changes from positive to negative in the neighborhood of an outline. Therefore, the outline specification means 13 specifies a position having positive response of the differential filter, as a first outline (target region) and a position having negative response, as a second outline (non-target region). The voxel selection means 14 selects voxels on the first outline and the second line, and the energy setting means 15 sets energy in such a manner that energy is minimized for a combination of the first outline at a position having positive response and the second outline at a position having negative response. Next, segmentation into the target region and the non-target region is performed by minimizing energy by using the labeling means 16, as described already. After then, an appropriate image, such as an image including only the target region, is generated, and the image is displayed on the display device by the display means 17.

Alternatively, when the shape is known to some extent, the outline estimation means 18 may estimate the outline of the target region based on image data by using a shape model represented by a predetermined parameter. For example, methods, such as ASM (Active Shape Model), are known. Main component analysis, independent component analysis and the like are performed on the shape of the target region, and an average shape and a vector for deforming the average shape are obtained. Further, the average shape is deformed to various shapes by changing the parameter of each vector. In this shape model, high order energy may be set for a corresponding outline position while various parameters are changed. At this time, it is more desirable that a voxel on the first outline in the target region and a voxel on the second outline in the non-target region (background) are selected with a constant space therebetween so that the outline is flexibly changeable.

In the aforementioned example, a circle is divided into plural arcs. Similarly, a shape model represented by a predetermined parameter may be divided into plural segments, and energy may be set for each segment.

In the method disclosed by C. Rother et al. in Non-Patent Document 2, the accuracy of region segmentation of a structure having a specific shape was able to be improved by using high order energy. Meanwhile, in the present disclosure, voxels are flexibly selected without inflexibly limiting to a shape like a rectangular window. Accordingly, it is possible to set sparse high order energy, and a solution is obtainable at high speed by a small amount of calculation. It is desirable that the method for selecting voxels is performed along the shape of the outline of a target of segmentation. For example, the outline of a blood vessel in a three-dimensional image has a circular cylinder. Therefore, a combination of voxels forming a circular shape is selected. When the outline shape of a target has been learned as a statistical model (for example, ASM), voxels along the outline of the model are selected. It is essential to select voxels along the outline of a target shape in this manner. The target structure may be any structure.

In the embodiments of the present structure, energy minimization has been described by using a graph cut method. The method should minimize a discrete function. Specific methods for minimizing energy are Graph Cuts, QPBO, Tree Reweighted Message Passing (please refer to V. Kolmogorov, "Convergent Tree-reweighted Message Passing for Energy Minimization", IEEE Transaction on PAMI, Vol. 28, Issue 10, pp. 1-16, 2006 for details) and the like. Further, a method for assigning labels to the target region and the non-target region, respectively, by using Graph Cuts is described in details in Y. Boykov and V. Kolmogorov, "An Experimental Comparison of Min-Cut/Max-Flow Algorithms for Energy Minimization in Vision", WEE Transaction on PAMI, Vol. 26, No. 9, pp. 1124-1137, 2004. Further, a method for assigning labels to the target region and the non-target region, respectively, by using QPBO is described in details in Non-Patent Document 2.

What is claimed is:

1. An image processing apparatus that performs labeling by assigning a first variable representing a target region and a second variable representing a non-target region, which excludes the target region, to each voxel constituting image data by using an energy minimization method, the image processing apparatus comprising:
   a memory configured to store a plurality of executable software instructions; and
   a hardware processor configured to execute the software instructions, which comprise:
   specifying a first outline that is present toward the target region and a second outline that is present at a position facing the first outline with an outline of the target region having a known shape between the first outline and the second outline, the first outline and the second outline having shapes similar to the known shape representing the outline of the target region;
   selecting an (i≥1) number of voxels forming the whole first outline and an (N−i) (N≥4, N−i≥1) number of voxels forming the whole second outline;
   when a condition that all of the i number of voxels of the first outline belong to the target region and all of the (N−i) number of voxels of the second outline belong to the non-target region is satisfied, setting N order energy to be smaller than the N-order energy when the condition is not satisfied; and
   labeling the target region or the non-target region by minimizing a discrete function including the N-order energy;
   wherein an energy function E is defined by adding a first order energy $E^k(x_k)$, a second order energy $E^{kl}(x_k, x_l)$ and the N-order energy $E^c(X_c)$ as the following expression:

$$E(x_1, \ldots, x_n) = \sum_{k \in V} E^k(x_k) + \sum_{k \in V, l \in Nk} E^{kl}(x_k, x_l) + \sum_{c \in C} E^c(X_c)$$

wherein V is a set of voxels constituting the image data, Nk is a set of voxels l adjacent to voxel k, c is a set of voxels constituting a high order energy, $X_c$ is a vector composed of variables of the set of voxels c, and C represents a set of c;
   wherein the first order energy $E^k(x_k)$ is set based on a label assigned to each voxel k that corresponds to variable $x_k$;
   wherein the second order energy $E^{kl}(x_k, x_l)$ is set based on labels assigned to two adjacent voxels x and l that correspond to variables $x_k$ and $x_l$ and, in a case in which one of the two adjacent voxels is located in the non-target region and the other of the two adjacent voxels is located in the target region, the second order energy $E^{kl}(x^k, x^l)$ is set to be smaller than the second order energy for other cases;
   wherein the N-order energy $E^c(X_c)$ is set as a value depending on labels assigned to voxels forming the first outline and the second outline that correspond to variables of vector $X_c$; and
   wherein binary labels assigned to the voxels constituting the image data are 0 and 1, the label 0 being assigned to the voxels in the non-target region, and the label 1 being assigned to the voxels in the target region.

2. The image processing apparatus, as defined in claim 1, wherein the specifying instructions specifies the first outline and the second outline in such a manner that the first outline and the second outline are apart from each other by a predetermined distance.

3. The image processing apparatus, as defined in claim 1, the software instructions further comprising:
   estimating the outline of the target region by using the image data,
   wherein the specifying instruction specifies the first outline and the second outline based on the estimated outline.

4. The image processing apparatus, as defined in claim 3, wherein the estimating instruction estimates the outline of the target region based on the image data by using differential filtering that can detect an edge.

5. The image processing apparatus, as defined in claim 3, wherein the estimating instruction estimates the outline of the target region based on the image data by using a shape model represented by a predetermined parameter.

6. The image processing apparatus, as defined in claim 1, wherein the setting instruction sets the same value for all the N-order energy when the condition is not satisfied.

7. The image processing apparatus, as defined in claim 1, wherein the labeling instruction uses Quadratic Pseudo-Boolean Optimization (QPBO) algorithm to minimize the discrete function including the N-order energy.

8. A non-transitory computer-readable recording medium having stored therein an image processing program that causes a computer to function as an image processing apparatus that performs labeling by assigning a first variable representing a target region and a second variable representing a non-target region, which excludes the target region, to each voxel constituting image data by using an energy minimization method, the image processing program executing the following instructions:
   specifying a first outline that is present toward the target region and a second outline that is present at a position facing the first outline with an outline of the target region having a known shape between the first outline and the second outline, the first outline and the second outline having shapes similar to the known shape representing the outline of the target region;
   selecting an (i≥1) number of voxels forming the whole first outline and an (N−i) (N≥4, N−i≥1) number of voxels forming the whole second outline;
   when a condition that all of the i number of voxels of the first outline belong to the target region and all of the (N−i) number of voxels of the second outline belong to the non-target region is satisfied, setting N order energy to be smaller than the N-order energy when the condition is not satisfied; and
   labeling the target region or the non-target region by minimizing a discrete function including the N-order energy;
   wherein an energy function E is defined by adding a first order energy $E^k(x_k)$, a second order energy $E^{kl}(x_k, x_l)$ and the N-order energy $E^c(X_c)$ as the following expression:

$$E(x_1, \ldots, x_n) = \sum_{k \in V} E^k(x_k) + \sum_{k \in V, l \in Nk} E^{kl}(x_k, x_l) + \sum_{c \in C} E^c(X_c)$$

wherein V is a set of voxels constituting the image data, Nk is a set of voxels l adjacent to voxel k, c is a set of voxels constituting a high order energy, $X_c$ is a vector composed of variables of the set of voxels c, and C represents a set of c;

wherein the first order energy $E^k(x_k)$ is set based on a label assigned to each voxel k that corresponds to variable $x_k$;

wherein the second order energy $E^{kl}(x_k, x_l)$ is set based on labels assigned to two adjacent voxels x and l that correspond to variables $x_k$ and $x_l$ and, in a case in which one of the two adjacent voxels is located in the non-target region and the other of the two adjacent voxels is located in the target region, the second order energy $E^{kl}(x^k, x^l)$ is set to be smaller than the second order energy for other cases;

wherein the N-order energy $E^c(X_c)$ is set as a value depending on labels assigned to voxels forming the first outline and the second outline that correspond to variables of vector $X_c$; and wherein binary labels assigned to the voxels constituting the image data are 0 and 1, the label 0 being assigned to the voxels in the non-target region, and the label 1 being assigned to the voxels in the target region.

9. An operation method of an image processing apparatus which performs labeling by assigning a first variable representing a target region and a second variable representing a non-target region, which excludes the target region, to each voxel constituting image data by using an energy minimization method, the operation method comprising:

specifying a first outline that is present toward the target region and a second outline that is present at a position facing the first outline with an outline of the target region having a known shape between the first outline and the second outline, the first outline and the second outline having shapes similar to the known shape representing the outline of the target region;

selecting an (i≥1) number of voxels forming the whole first outline and an (N−i) (N≥4, N−i≥1) number of voxels forming the whole second outline;

when a condition that all of the i number of voxels of the first outline belong to the target region and all of the (N−i) number of voxels of the second outline belong to the non-target region is satisfied, setting N order energy to be smaller than the N-order energy when the condition is not satisfied; and labeling the target region or the non-target region by minimizing a discrete function including the N-order energy;

wherein an energy function E is defined by adding a first order energy $E^k(x_k)$, a second order energy $E^{kl}(x_k, x_l)$ and the N-order energy $E^c(X_c)$ as the following expression:

$$E(x_1, \ldots, x_n) = \sum_{k \in V} E^k(x_k) + \sum_{k \in V, l \in Nk} E^{kl}(x_k, x_l) + \sum_{c \in C} E^c(X_c)$$

wherein V is a set of voxels constituting the image data, Nk is a set of voxels l adjacent to voxel k, c is a set of voxels constituting a high order energy, $X_c$ is a vector composed of variables of the set of voxels c, and C represents a set of c;

wherein the first order energy $E^k(x_k)$ is set based on a label assigned to each voxel k that corresponds to variable $x_k$;

wherein the second order energy $E^{kl}(x_k, x_l)$ is set based on labels assigned to two adjacent voxels x and l that correspond to variables $x_k$ and $x_l$ and, in a case in which one of the two voxels is located in the non-target region and the other of the two adjacent voxels is located in the target region, the second order energy $E^{kl}(x^k, x^l)$ is set to be smaller than the second order energy for other cases;

wherein the N-order energy $E^c(X_c)$ is set as a value depending on labels assigned to voxels forming the first outline and the second outline that correspond to variables of vector $X_c$; and wherein binary labels assigned to the voxels constituting the image data are 0 and 1, the label 0 being assigned to the voxels in the non-target region, and the label 1 being assigned to the voxels in the target region.

10. The image processing apparatus, as defined in claim 1, wherein the labeling instruction uses a Graph Cuts algorithm to minimize the discrete function including the N-order energy.

\* \* \* \* \*